US009524371B2

(12) United States Patent
Osband et al.

(10) Patent No.: US 9,524,371 B2
(45) Date of Patent: *Dec. 20, 2016

(54) SYSTEM AND METHOD FOR FACILITATING THE COLLECTION, ANALYSIS, USE AND MANAGEMENT OF CLINICAL ANALYTICS RESULTS TO IMPROVE HEALTHCARE

(71) Applicant: TriZetto Corporation, Denver, CO (US)

(72) Inventors: Gerald E. Osband, Scottsdale, AZ (US); Rosalind Elaine Therrien, Merrimack, NH (US); Ivana Naumovic, Denver, CO (US); Scott Johnson, Wheaton, IL (US)

(73) Assignee: TriZetto Corporation, Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/749,133

(22) Filed: Jun. 24, 2015

(65) Prior Publication Data
US 2015/0294070 A1 Oct. 15, 2015

Related U.S. Application Data

(63) Continuation of application No. 13/600,540, filed on Aug. 31, 2012, now Pat. No. 9,075,869.

(51) Int. Cl.
G06F 17/30 (2006.01)
G06F 19/00 (2011.01)
(Continued)

(52) U.S. Cl.
CPC ....... *G06F 19/322* (2013.01); *G06F 17/30563* (2013.01); *G06F 17/30684* (2013.01);
(Continued)

(58) Field of Classification Search
CPC ...... G06Q 50/24; G06Q 50/22; G06Q 10/063; G06F 17/30657; G06F 17/30563; G06F 17/30684; G06F 19/322
(Continued)

(56) References Cited

U.S. PATENT DOCUMENTS 5,544,044 A    8/1996  Leatherman ............ 364/401
5,867,821 A *  2/1999  Ballantyne ........ G06F 19/327
                                                    705/2
(Continued)

OTHER PUBLICATIONS

Osband, Jerry, "Population Health Management, Informed by Clinical Analytics, Can Bend Cost Trend and Improve Outcomes," *Managed Care*, vol. 24, No. 23, 3 pp., Dec. 1, 2011.

Primary Examiner — Thanh-Ha Dang
(74) Attorney, Agent, or Firm — Dawn-Marie Bey; Bey & Cotropia PLLC

(57) ABSTRACT

Systems and process for performing analytical processes on the health-related data for a person include components and steps for processing system multiple files from multiple sources containing health-related data for numerous individual. Such processing may include: staging health-related data; matching pieces of staged data to a person using one or more matching rules; compressing the matched staged data for the person into a compressed file through assignment of a universal identifier which is associated with the person; providing the compressed file to an analytics engine; and decompressing the at least one analytics results file using universal identifier to access the analytics results for the person. Additionally, the analytics results for the person may be provided to a user for intervention into the health of the person.

18 Claims, 4 Drawing Sheets

(51) Int. Cl.
*G06Q 50/24* (2012.01)
*G06Q 50/22* (2012.01)
*G06Q 10/06* (2012.01)

(52) U.S. Cl.
CPC .......... *G06F 19/345* (2013.01); *G06Q 50/24* (2013.01); *G06F 17/30657* (2013.01); *G06Q 10/063* (2013.01); *G06Q 50/22* (2013.01)

(58) Field of Classification Search
USPC .................. 707/731, 737, 763, 783, 748
See application file for complete search history.

(56) References Cited

U.S. PATENT DOCUMENTS

| | | | | |
|---|---|---|---|---|
| 6,611,846 | B1 * | 8/2003 | Stoodley | G06F 19/322 705/3 |
| 6,820,235 | B1 * | 11/2004 | Bleicher | G06F 19/325 600/300 |
| 7,174,335 | B2 * | 2/2007 | Kameda | G06F 19/322 |
| 7,711,577 | B2 | 5/2010 | Dust et al. | 705/2 |
| 7,788,202 | B2 | 8/2010 | Friedlander et al. | 706/47 |
| 7,801,591 | B1 * | 9/2010 | Shusterman | A61B 5/0205 600/300 |
| 8,001,071 | B2 * | 8/2011 | Jordan | G06N 5/04 706/47 |
| 8,036,916 | B2 | 10/2011 | Dust et al. | 705/2 |
| 8,099,303 | B1 * | 1/2012 | Battaglia | G06F 19/328 705/2 |
| 8,121,864 | B2 * | 2/2012 | Green | G06Q 10/109 705/3 |
| 8,126,739 | B2 * | 2/2012 | Green | G06Q 10/109 705/3 |
| 8,311,848 | B2 * | 11/2012 | Subash | G06F 19/322 705/2 |
| 8,527,291 | B1 * | 9/2013 | Kochendorfer | G06Q 10/10 705/2 |
| 8,583,454 | B2 * | 11/2013 | Beraja | G06Q 50/00 705/2 |
| 8,645,424 | B2 * | 2/2014 | Miller | G06F 19/3418 707/781 |
| 8,892,571 | B2 | 11/2014 | Friedlander et al. | 707/748 |
| 9,075,869 | B1 * | 7/2015 | Osband | G06F 17/30684 |
| 2002/0026332 | A1 | 2/2002 | Snowden et al. | 705/3 |
| 2003/0037054 | A1 * | 2/2003 | Dutta | G06F 19/322 |
| 2004/0078228 | A1 | 4/2004 | Fitzgerald et al. | 705/2 |
| 2005/0222875 | A1 * | 10/2005 | Lordeman | G06F 19/328 705/3 |
| 2006/0080312 | A1 * | 4/2006 | Friedlander | G06F 19/322 |
| 2006/0101063 | A1 * | 5/2006 | Schreeder | G06F 19/328 |
| 2006/0271401 | A1 | 11/2006 | Lassetter et al. | 705/2 |
| 2007/0244714 | A1 * | 10/2007 | McCluskey | G06Q 10/06393 705/2 |
| 2008/0046292 | A1 * | 2/2008 | Myers | G06F 17/30557 705/3 |
| 2008/0086337 | A1 * | 4/2008 | Soon-Shiong | G06Q 10/00 705/3 |
| 2009/0150185 | A1 * | 6/2009 | Lassetter | G06F 19/322 705/3 |
| 2009/0228304 | A1 * | 9/2009 | Ciarniello | G06F 19/327 705/3 |
| 2009/0248445 | A1 | 10/2009 | Harnick | 705/3 |
| 2011/0004488 | A1 | 1/2011 | Benja-Athon | 705/2 |
| 2011/0066446 | A1 | 3/2011 | Malec et al. | 705/2 |
| 2011/0225006 | A1 * | 9/2011 | Manning | G06Q 30/01 705/2 |
| 2011/0270632 | A1 * | 11/2011 | Manning | G06F 19/327 705/3 |
| 2011/0288877 | A1 * | 11/2011 | Ofek | G06F 19/322 705/2 |
| 2012/0010898 | A1 | 1/2012 | Dust et al. | 705/2 |
| 2012/0185275 | A1 * | 7/2012 | Loghmani | G06F 19/328 705/3 |
| 2013/0066650 | A1 * | 3/2013 | Ackerman | G06F 19/328 705/2 |
| 2013/0197940 | A1 | 8/2013 | Garber | 705/3 |
| 2013/0332189 | A1 * | 12/2013 | Manning | G06F 19/363 705/2 |

* cited by examiner

SYSTEM AND METHOD FOR FACILITATING THE COLLECTION, ANALYSIS, USE AND MANAGEMENT OF CLINICAL ANALYTICS RESULTS TO IMPROVE HEALTHCARE

CROSS REFERENCE TO RELATED APPLICATIONS

This application is a continuation of U.S. patent application Ser. No. 13/600,540, filed Aug. 31, 2012, entitled "System and Method For Facilitating the Collection, Analysis, Use and Management of Clinical Analytics Results to Improve Healthcare," which is incorporated hereby by reference.

FIELD OF EMBODIMENTS

Embodiments are directed to systems and methods for facilitating improvement of the healthcare status of individuals and populations through use of clinical analytics while improving quality and costs, which results in decreased overall trends of healthcare spending.

BACKGROUND AND SUMMARY OF PROBLEM

Clinical analytics may be defined as a set of methodologies, tools, and information technology infrastructure that transforms raw healthcare data into meaningful and useful information, knowledge, and visualization that enables effective insights and decision-making for clinical users. In practice, it has proven to be difficult to actually make effective use of the resulting clinical analytics data to improve health-related outcomes. Further, the analytics are only as good as the accuracy of the incoming data. In the healthcare field, comprehensive and accurate data regarding a person's health-related history is critical to the generation of useful analytics results. Efforts to assure continuity of care, accurate record keeping, effective follow-up and preventive care, prompt payment, and detection of fraud, waste, and abuse all would benefit from the availability of accurate analytics. A particular challenge to analytics accuracy arises because the gamut of personal attributes commonly used to identify a person (for example, name, birth date, and sex) is rarely captured in the same manner by each entity in the health care system; accordingly, rarely is comprehensive health-related data for the same individual actually attributed to that individual. Identification of proper records is key to the generation of useful analytics. Accordingly, there is a specific need for a process that allows for the rapid and accurate identification of the proper records and their integration for the purpose of providing high quality, patient-focused care.

Further, while there are tools and vendors for performing analytics on available data, including data management, stratification and predictive modeling, technical challenges remain with respect to the availability of data for performing analytics, as well as the significant challenge which exists for payers attempting to actually integrate the resulting analytics data into care management solutions. Exemplary analytics vendors include, for example, MEDai (an Elsevier company at the time of filing of this application). Accordingly, there is a need for systems and processes that effectively integrate medical data sources with analytics capabilities to provide both data-in and data-out solutions that are useful for a range of recipients to improve health-related outcomes.

SUMMARY OF EMBODIMENTS

In a first embodiment, a process for performing analytical processes on the health-related data for a person includes: receiving at a first processing system multiple files from multiple sources containing health-related data for a person; staging by the first processing system the health-related data from the multiple files into at least one database in accordance with one or more categories associated with the multiple files; matching by the first processing system at least two pieces of staged data from the multiple files to a single individual using one or more matching rules; compressing by the first processing system the matched staged data for the single individual into at least one compressed file, wherein each piece of the matched staged data in the at least one compressed file is assigned the same universal identifier and the universal identifier is associated with the same single individual; providing the at least one compressed file to an analytics engine for performing one or more predetermined analytical processes thereon and creating at least one analytics results file therefrom; receiving by a second processing system the at least one analytics results file from the analytics engine and decompressing the at least one analytics results file using universal identifier to access the analytics results for the single individual; and providing access to the analytics results for the single individual to at least one user, wherein the user utilizes the analytics results in a process related to the health of the single individual.

In a second embodiment, a system for performing analytical processes on the health-related data for a person includes: a first processing system for receiving multiple files from multiple sources containing health-related data for a person, staging the health-related data from the multiple files into at least one database in accordance with one or more categories associated with the multiple files, matching at least two pieces of staged data from the multiple files to a single individual using one or more matching rules, compressing the matched staged data for the single individual into at least one compressed file, wherein each piece of the matched staged data in the at least one compressed file is assigned the same universal identifier and the universal identifier is associated with the same single individual and providing access to the at least one compressed file; an analytics engine for accessing the at least one compressed file, performing one or more predetermined analytical processes thereon and creating at least one analytics results file therefrom; a second processing system for accessing the at least one analytics results file from the analytics engine, decompressing the at least one analytics results file using the universal identifier to access the analytics results for the single individual and providing access to the analytics results for the single individual to at least one user, wherein the user utilizes the analytics results in a process related to the health of the single individual.

SUMMARY OF FIGURES

The following Figures are intended to further describe the embodiments discussed herein and are to be considered in conjunction with the description herein.

DETAILED DESCRIPTION OF EMBODIMENTS

Figure 1A:
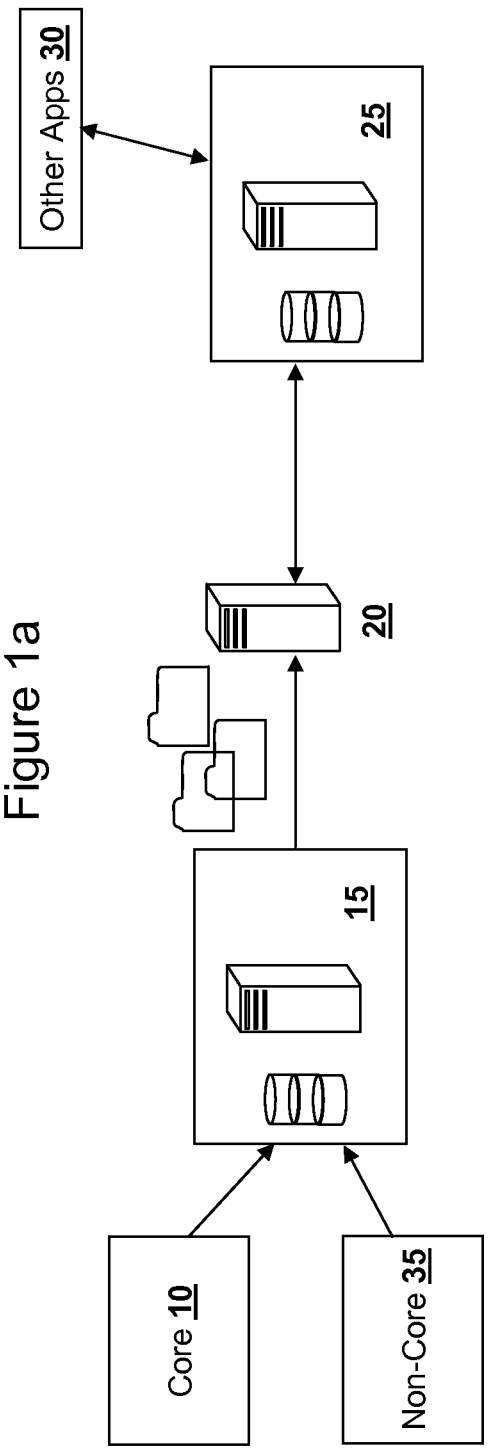
FIGS. 1a and 1b are exemplary system configurations for performing the processes described herein.
Figure 1B:
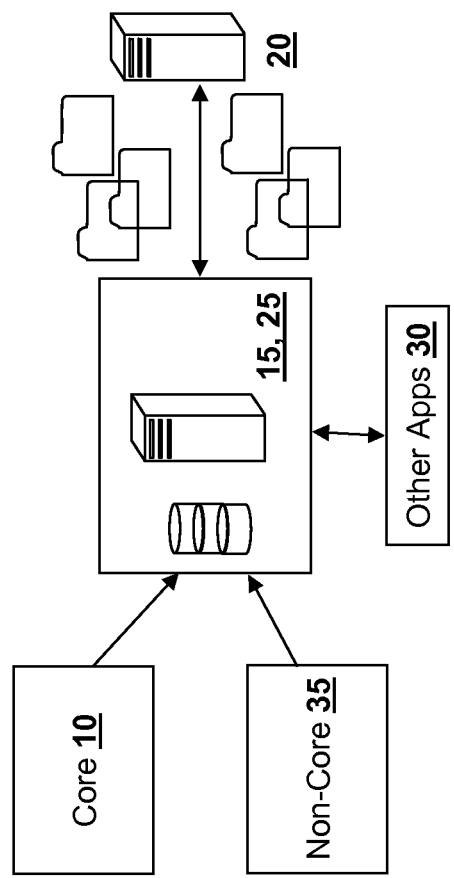

Referring to FIGS. 1a and 1b, the embodiments described herein are directed to a system architecture that may include: one or more core subsystems 10 which generate health-related medical claim files (hereafter core data files) for processing by a payer; one or more staging subsystems 15 for receiving the core data files and extracting information therefrom in accordance with staging requirements for an analytics engine; an analytics engine 20 for performing various analytics analyses on received staged data; and an interface subsystem 25 for facilitating two-way flow of data/analytics results from/to one or more other applications 30, e.g., TriZetto Clinical CareAdvance, to the analytics engine 20. The interface subsystem 25 may include an application programming interface (API) and other processing capabilities for formatting and translating data for use by the analytics engine and/or other applications. Additionally, the system architecture may also include one or more non-core subsystems 35, e.g., laboratory, pharmacy, biometric and health risk assessments (HRAs) data sources (hereafter non-core data files), that export the non-core data files to the analytics engine 20 by way of the staging subsystems 15 for inclusion in the analyses. In accordance with various specific applications of the analytics engine vendor, specifically formatted analytics data may be available to one or more plans, payers, providers and other care-related entities.

In an exemplary embodiment, the staging subsystem 15 includes one or more processing applications running on one or more designated servers and one or more staging databases, for receiving core and non-core data files, extracting and staging data therein and presenting to the analytics engine 20. Additionally, although shown separately in FIG. 1a, staging subsystem 15 and interface subsystem 25 may utilize overlapping resources, e.g., servers and storage, as shown in FIG. 1b. The extracted core data may include, but is not limited to: member data, eligibility data, provider data, claims data, group data. The extracted non-core data may include, but is not limited to, laboratory, pharmaceutical (i.e., prescription), biometric, health assessment and other health-related data for members. After the analytics is performed on the staged data, the results may be submitted to one or more care-related entities and/or other applications 30 for additional analysis in accordance with desired goals. For example, analytics output from the analytics engine 20 may be integrated back to other applications 30 (e.g., TriZetto Clinical CareAdvance, TriZetto Value-Based Benefits, TriZetto Value Based Reimbursement applications).

Figure 2:
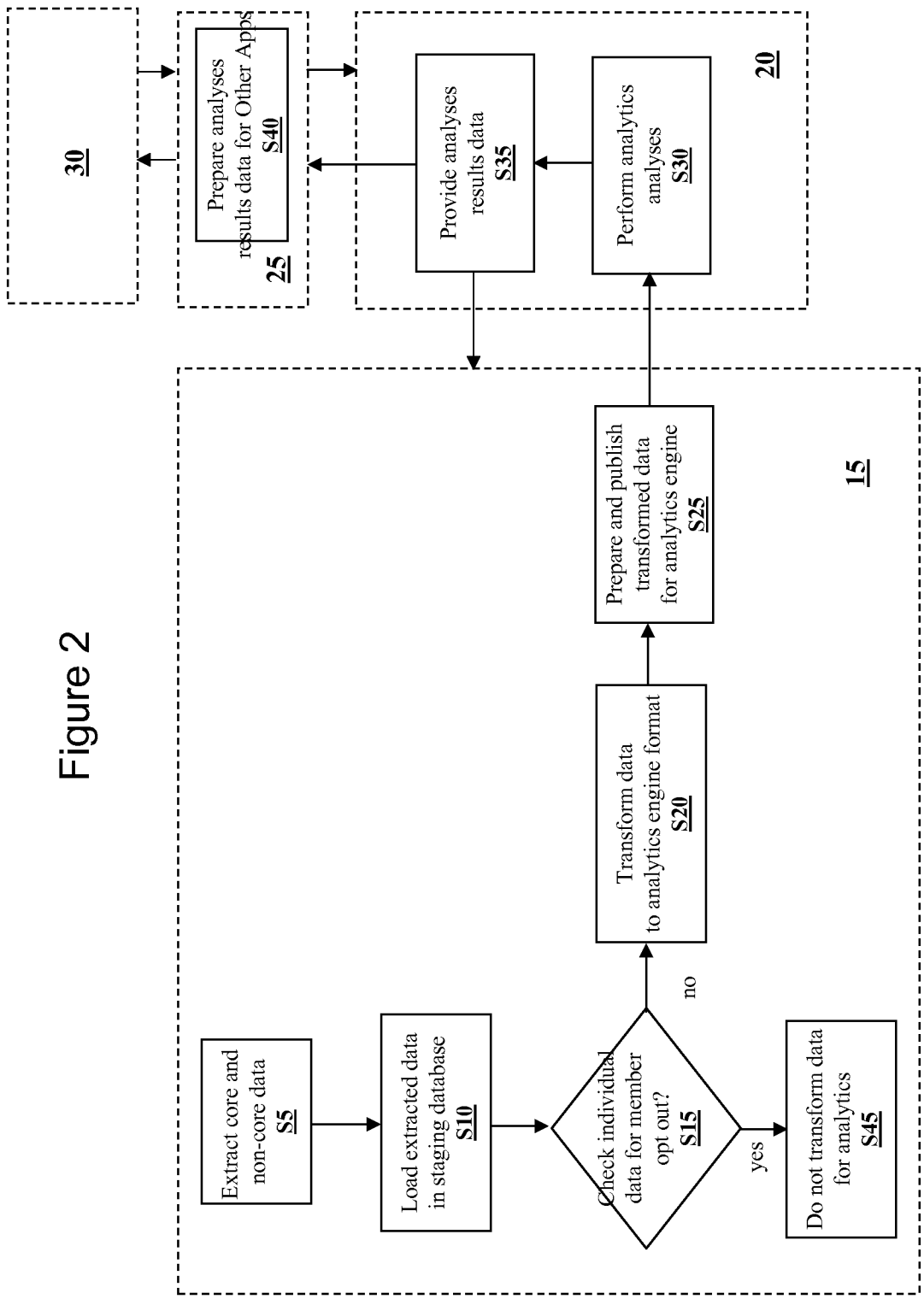
FIG. 2 is a process schematic and flow in accordance with the embodiments described herein.

Referring to FIG. 2, a high level process flow in accordance with an embodiment of the present invention includes the following steps: at staging subsystem 15, core and non-core data is extracted S5, extracted data is loaded into one or more staging tables S10, individual data is checked for member opt out S15 and if the member has opted out, that data is not transformed for analytics processing S45. If the member has not opted out, the staging subsystem 15 transforms the data to a format for processing by the analytics engine S20 and publishes the transformed data for use by the analytics engine S25. The analytics engine 20 receives the published data and performs analytics analyses thereon S30. The results of the analyses are provided to one or more subsystems 15, 25 for use in specific applications. For example, referring back to FIGS. 1a and 1b, interface subsystem 25 performs additional actions, e.g., conversions, parsing, translation, extraction, formatting, in order to ready the analyses results data S40 for use in Other Applications 30. Such additional actions may include the creation of results files by Members, Gap, episode treatment groups (ETGs), etc. Other Applications 30 include software-based applications including tools for aiding with disease, case and utilization management. Users of Other Applications include providers, health plans and members. One such exemplary Other Application is TriZetto's CareAdvance suite, including Clinical CareAdvance, CareAdvance Provider and Personal CareAdvance. Additionally, the Other Applications 30 may represent an additional data source and as such, data from the Other Applications 30 may flow back to the analytics engine and improve the accuracy of the analyses results data.

The core data may be extracted by the staging subsystem 15 either on a pre-set schedule or on-demand from the core subsystems 10. This extraction could be a push action, wherein the core subsystems send the data to the staging subsystems on schedule or alternatively the extraction could be a pull action, wherein the staging subsystems affirmatively request the data from the core subsystems on a schedule or on demand. Similarly, for the non-core data, the staging subsystem 15 may receive data pushes from the non-core subsystems 35 or via a pull action, wherein the data is requested from the non-core subsystems. The staging subsystem has the ability to support core data import where a customer is using two or more instances of a core system at the same time as discussed further below.

More specifically, it is understood that core systems may structure data and data processing runs in logical units, e.g., by customer or other logical levels in accordance with the customer data. For example, a single customer may have multiple subclients, e.g., a single payer could support multiple lines of business such as commercial, HMO (health maintenance organization), Medicare plans and the like. Since the data organization and analyses differ depending on the line of business, the core system's software functionality treats these "subclients" as different logical instances or logical units of analysis. Importantly, a single Member (and individuals associated therewith) could have data across multiple subclients. In the present embodiments, the staging subsystems 15 are able to intake multiple logical instances from the core systems process, transform and send a single data file per swimlane (e.g., Groups, Members, Networks, Provider, Claims) to the analytics engine 20. And as discussed further herein, the interfacing subsystem 25 is able to intake a single results file per return swimlane (e.g., Member, Risk) from the analytics engine 20, and is able to unpack and transform it into usable datafeeds for Other Applications 30, such that the Other Applications 30 know which subclient the Member is coming from.

Ultimately, the customers or end-users of the Other Applications 30 will be able to view Member (individual) matching per subclient or Member (individual) matching across all subclients as needed. For the latter, the Members (and individual persons associated therewith) likely have completely separate and unique subclient identifiers associated therewith and these unique identifiers do not change, except when the Members and associated data are matched and consolidated with a UMID (unique member identifier) for analytics purposes as discussed herein. Throughout the processes, reference tables are maintained so that the Members and data can be attributed accurately across the customers, subclients and Members.

Additionally, the staging subsystem 15 may refresh subsets of core data at predetermined intervals, e.g., the files may be refreshed monthly, the Gap file weekly to produce incremental results or on an ad-hoc basis.

The staging subsystem is able to group data from varied sources in accordance with the member, or more particularly, the individual, to which the data applies in accordance with a unique member identification and matching process (UMID process). This process will evaluate core data in order to identify records that belong to the same physical person. In addition to facilitating the matching functionality itself against the records in the staging subsystem 15 database, this process also facilitates defining of the matching criteria by a customer, establishes matching logic based on the selected criteria, and establishes verification processing rules, e.g., confidence level criteria.

The process assigns an identifier ("ID") to each member record that will uniquely identify an individual person so that all information about that person can be associated with the person, not just the member record. The UMID process has the following attributes and functions. A unique identifier is assigned to every individual member coming from a core system to the staging subsystem 15. In other words, every individual person has a unique identifier which can be used to reliably associate all information about that person. Accordingly, multiple records for a member can be associated with a single unique member identifier (UMID). There is a persisted cross-reference of the unique identifier along with identification/intrinsic data from other systems. This intrinsic data includes internal system identifiers used to identify the member on other systems. Associative information for a member that exists in core and non-core systems may be used to successfully match records to the UMID. Such associative information generally includes name, date of birth (DOB), social security number (SSN), address and zip code. Additionally, the matching process allows for the use of varied attributes to perform the identification. Such varied groups of attributes can be used to positively identify a person, depending on the best associative information available in the source system. For example, and as discussed below, an attribute group can be First Name+Last Name+SSN+Date of Birth for a positive match. In a system where SSN is not populated because of privacy concerns, another attribute group that can be used for a match is Last Name+DOB+Medicare ID+Zip code. These attribute groups are configurable on a client to client basis. The process implements evaluation of confidence level of matching and allows implementation-level tuning of identification and matching methods. Additionally, while the matching process is generally performed by a processor in accordance with rules programming, there may be manual intervention for "gray-area" members and related data. This manual intervention may include a process for flagging the gray-area pieces of data for consideration and formal action by an administrator in regards to assigning or unassigning a UMID.

Examples of match attributes, i.e., data elements, that can be used to create match rules include, but are not limited to: First Name; Last Name; Gender; social security number (SSN) or a portion thereof; Date of Birth (DOB) or a portion thereof; Title; Marital Status; Group Name; Subscriber ID; Relation to Subscriber (Code); Status Code; Language Code; Medicare No.; Medicaid No.; Familylink ID; Home Address information; and mailing address information. Exemplary matching rules may include, but are not limited to:

Last Name+First Name+Gender+DOB+SSN

Last Name+First Name+DOB+Zip+last 4 characters of SSN

Last Name+First Name+Birth Year+Zip

Last Name+First Name+DOB+Gender+SSN+Zip

Last Name+First Name+SSN

Last Name+First Name+DOB+Gender

Last Name+First Name+DOB+Zip

Last Name+DOB+Gender+SSN+Zip

Last Name+SSN

Figure 3:
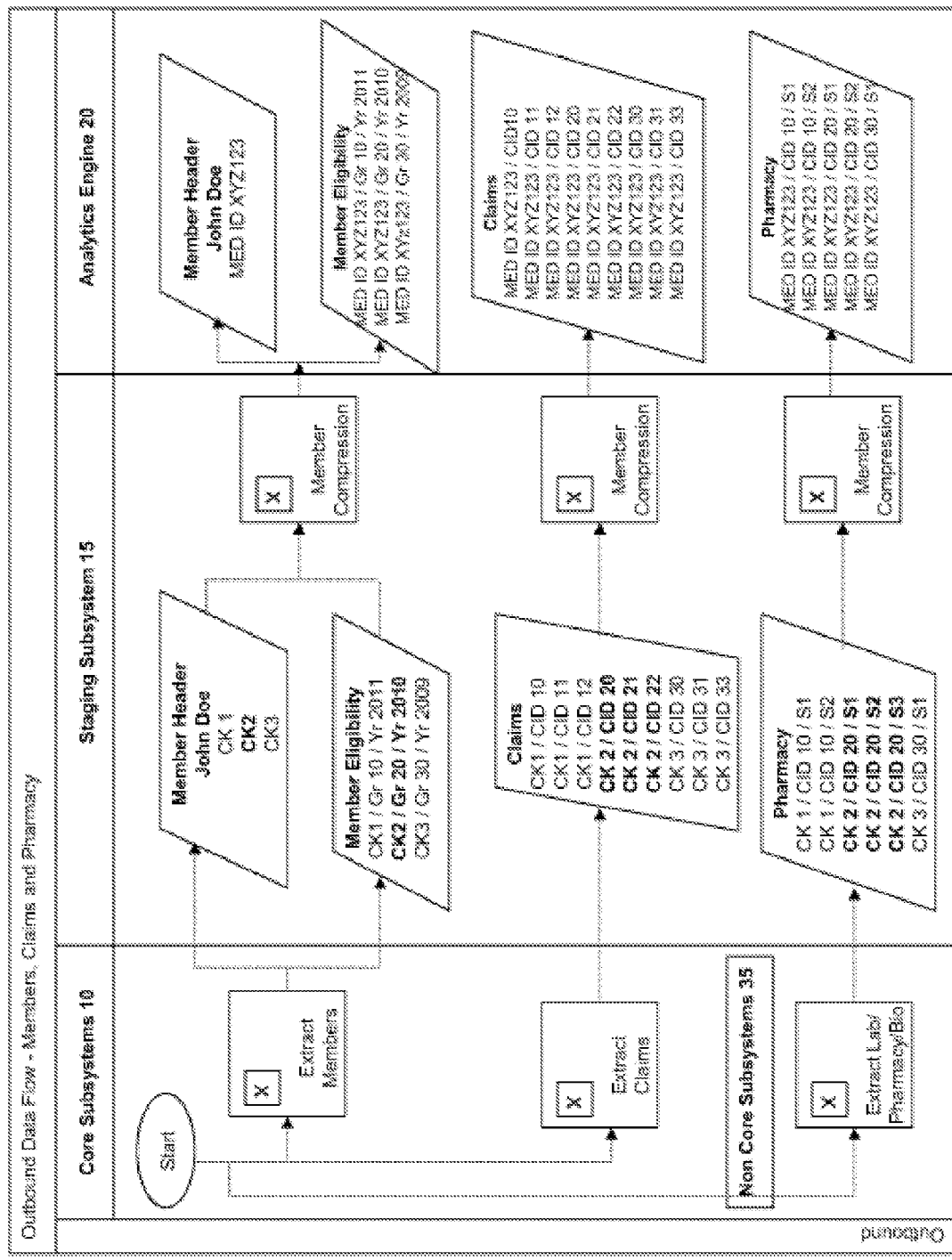
FIG. 3 is a process and data structure schematic and flow in accordance with the embodiments described herein.

Since the analytics engine 20 is performing analysis for individual persons, it is critical that the data input to the analytics engine be correctly associated by person for the same person. Accordingly, the staging subsystem 15 implements the UMID process against all incoming member records and in some cases compresses multiple member records, claim data and other data (lab/pharmacy/bio) received from the same (or different) core and non-core systems into a single person designated by UMID. An exemplary data flow scenario to the analytics engine as described herein is shown in FIG. 3, wherein member, claim and non-core data, i.e., laboratory, pharmacy and bio screening data is extracted (push or pull) to the staging subsystem which performs a series of operations on the data in order to determine member name, member eligibility, member claims and member non-core data and match data within that member data with a person. By applying one or more of the matching rules of the UMID process to the member information, compressed data files are generated for persons and the associated person data is identified through a universal identifier that remains with the data through the analytics engine. Compression of data into files for persons is required because members and persons are not necessarily the same entity.

The following example is instructive. Spouse A has Plan A coverage for her entire family which includes Spouse B, Child A and Child B for years 2009 to 2011. Spouse A, Spouse B, Child A and Child B are all individuals who are covered under Plan A and generate instances of core and non-core data during 2009-2011. All of these instances of data generated by all of these persons, Spouse A, Spouse B, Child A and Child B, is identified to/by Plan A through the member, Spouse A. Accordingly, what the staging subsystem does is parse Spouse A's incoming member data and attribute or assign the data more accurately in accordance with the generating individual, i.e., Spouse A, Spouse B, Child A or Child B. Then all core data for each individual is compressed into a claim file for that individual and non-core data for each individual is compressed into a non-core file for that individual and the compressed data is assigned a unique identifier that traces back to the individual and is also able to be associated with the member (policy holder), i.e., the member's plan. This individualized data is then presented to the analytics engine to analyze for specific issues, e.g., gaps in care, episode treatment groups (ETGs), trends, etc.

Table 1 below includes an exemplary listing of the type of member predictive analytics that may be performed by the analytics engine using inputted data. This listing is not exhaustive.

TABLE 1

| Measure Name | Description |
| --- | --- |
| Forecasted Cost | Forecasted amount ($) per member |
| Risk Level | Risk level 1 through 5. The members (active and inactive) are ranked by forecasted cost and assigned to a percentile with the members at greatest risk assigned to percentile100. |
| Prediction Rank | Rank 1-100. |
| Prescription (Rx) Forecasted Dollars | Rx Forecasted Dollars |
| Rx Rank | Forecasted Rx Cost rank, 1-100 |
| Emergency (ER) Forecasted visits | Forecasted ER visits for the member |
| ER Rank | Forecasted ER Visits prediction rank, 1-100 |
| Inpatient Forecasted days | Forecasted inpatient days for the member |
| Inpatient Rank | LOS days prediction rank, 1-100. |
| Chronic Impact Score | This score ranks the member according to the potential reduction in diagnosis-based cost for guideline gap diseases. |
| Acute Impact Score | This score ranks the member according to the potential acute care component (ER and inpatient activity) of their predicted cost. |
| Forecasted Risk Index | Forecasted Risk Index is equal to the Total Forecasted Cost of the individual member divided by the Average Forecasted Cost for all members. |
| Motivation Index | Score related to the member's motivation to change |

Further, the analytics engine may identify gaps in patient care. Some exemplary gap measures covering common health and wellness conditions include, but are not limited to: HBA1C testing twice per year for Diabetes; Diuretic plus serum chemistry panel or potassium for CHF; Protime/INR: +/−30 days from current warfarin or indandione prescription for CVA; Lipid lowering medications for Hyperlipidemia; Spirometry/pulmonary function testing for Asthma; Theophylline plus theophylline level testing for COPD; Myocardial infarction and beta-blocker for CAD; Colon cancer screening: Age 50 and older; and Glaucoma screen: adults >=65.

Further still, the analytics engine may identify Episode Treatment Groups (ETGs), i.e., disease conditions assigned to a person based on incoming data associated with the person. Exemplary, but not limiting ETGs include: Cardiovascular Surgery ETG; Cardiovascular Medical ETG; Asthma ETG; Bronchitis ETG; and Dermatological ETG.

In a specific implementation of the data flow process of FIG. 3, the staging subsystem includes functionality for the preparation and delivery of a UMIDMembers file to the UMID processing component. The UMIDMembers file contains all members that exist in the MemberPerson table generated by the core system. The UMIDMembers file or a separately dropped trigger file will include information that triggers the UMID processing of the UMIDMembers file. Each record in the UMIDMembers file is processed, one at a time, executing each rule in order of precedence until a determination is made; that is, either a match is found and the record being processed is assigned an existing UMID or a match is not found and a new UMID is assigned. The first attempt at a match, though not defined in the rules configuration, will always be by the combination of SystemID/MemberKey. A SystemID/MemberKey is an internal system ID for a member that uniquely identifies a member within an individual system only. Generally, this ID is not visible to customers, but can be shared among participating systems. If a match is found in the UMID database, the UMID along with all the data on the incoming record will be stored to the Results table and this record processing is completed. If a match on SystemID/MemberKey was not found, processing continues through each match rule, in order of precedence.

If a match is found based on an Auto-Match rule, the results will be stored to the UMID table(s) and also written to a Results table. If a match is found based on a Review rule, the incoming record will be stored temporarily so that the customer can review these records through the user interface and make a match or no-match determination. The UMID component will process all members from the incoming file before processing is considered complete. In other words, processing is not complete until every record from the incoming UMIDMembers file has a UMID and exists in the Results table or has been written to the table for member match review. When the UMID process results are complete, the results are loaded into a separate share table in accordance with the UMID (Unique Id) and the corresponding Member Id (MemberKey). Multiple member records representing the same person (Unique ID) will be combined in the Membership file that is sent to the analytics engine.

Figure 4:
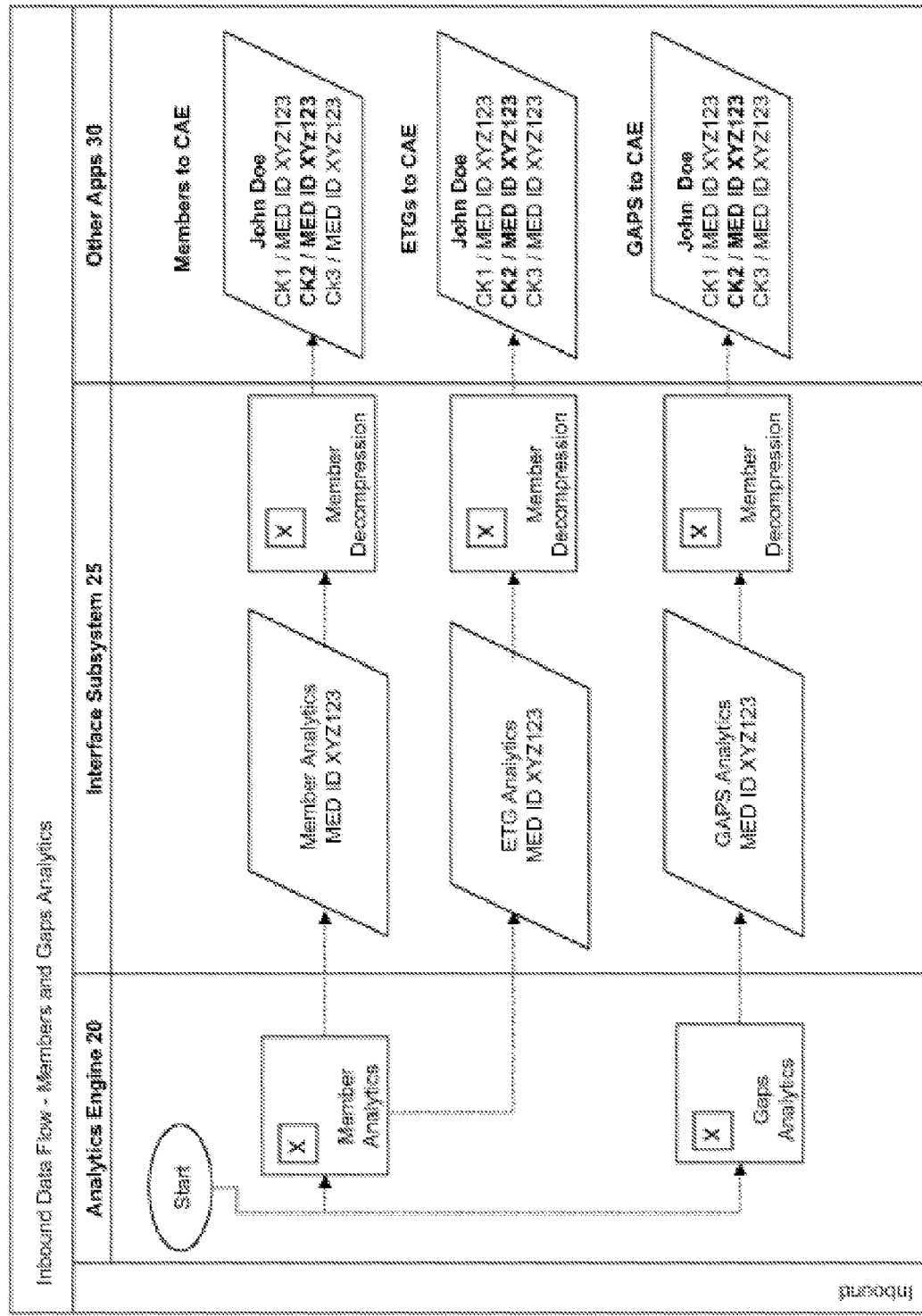
FIG. 4 is a process and data structure schematic and flow in accordance with the embodiments described herein.

Referring to FIG. 4, analytics files from the analytics engine 20 are exported (push/pull) to an interface subsystem 25 where they are de-compressed to obtain the member, and ultimately the individual information, that can be used by Other Applications 30. As was noted above, while the staging and interface subsystems are shown as being separate in the figures, these could be the same subsystem or, preferably, subsystems within a larger system that may or may not also include control over the analytics engine and/or Other Applications.

In a specific implementation of the data flow process of FIG. 4, the analytics results are joined by individual staging tables, i.e., Members, Gaps and ETG, to the share table by Uniqueid and all MemberKey(s) assigned to that Uniqueid are identified. For every MemberKey returned for the Uniqueid, the table row is replicated with the Uniqueid, replacing the Uniqueid with the MemberKey. This replication of rows, i.e., decompression, occurs for each of the files that is to be exported to one or more Other Applications, e.g., Members, Gaps and ETG.

There is no requirement that members allow their data to be analyzed by the analytics engine. The present embodiments provide functionality for members to opt-out of the processes described herein. Alternatively, member data may be analyzed on a completely anonymous basis. That is, for members who have requested privacy opt-out, the Member row may be maintained in the datafeed but all personal health information (PHI) data including, but not limited to, physical and mailing address, email, phone numbers, date-of-birth (DOB), social security number (SSN), parent or guardian ID, gender, ethnicity, disability status, marital status, claim information, utilization management (UM) information, diagnosis history and the like is removed.

Users of the Other Applications 30 receiving the analytics results data are able to apply the results data in numerous situations to improve member health in a variety of ways, from course of medical treatment to efficient workload management of health professionals. The following examples are instructive.

In a first exemplary use case, the results data is used to help asses a member's needs. For example, a nurse is sent information on triaging a member based on rules that are fired for auto-triaging that member. The nurse reviews the case history, but in order to get the best picture of the member before making her first call, she also reviews the analytics results data for the member. If, for example, the nurse notices that the member was also identified as being high risk for inpatient admission, has coronary artery disease, high blood pressure, and has gaps in care because she is not on evidence-based medicine (EBM) recommended medications to manage her conditions, this information would likely impact how the nurse directs the care for the member. The next steps in care would likely be different in view of the available analytics results data.

In a second exemplary use case, the availability of gaps in care analytics data may be used to auto-triage a member to a particular health care professional and add the relevant member information to the health care professional's work queue.

In a third exemplary use case, analytics data is useful in prioritizing work load based on member health details. For example, in instances where multiple members are in a nurse's work queue, member analytics data could assist the nurse with determining which member to assist first. Take the specific case where a member in the queue needs case management after suffering a stroke. The analytics data indicates that future risk for the member was high prior to the stroke; the member would likely be addressed first.

Further still, analytics data aids a workflow manager with the assignment of cases to individual case managers. The workflow manager uses analytics data such as gaps in care and risk to assess each individual case manager's assigned cases. The workflow manager then decides if any adjustments need to be made and distributes new assignments based on staff availability and individual work load capacity. The analytics data is useful in helping the case manager determine the acuity level of the cases assigned and the equitable distribution of work load. The analytics data (such as gaps in care and risk) is a good indicator of the potential work effort or new case assignments.

The invention claimed is:

1. A process for transforming health-related data for an individual from multiple sources in preparation for health-related analytical processing thereof comprising:
    extracting by a first processing system core data files from a core system, the core data files containing medical claims payment data which is separately processed by the core system to determine payment by a payer to a medical service provider for medical services provided to the individual, wherein the core data files also contain first health-related data for the individual;
    loading by the first processing system the extracted core data files, including the first health-related data for the individual, into a staging database;
    determining whether the individual has opted out of analytical processing of any portion of the first health-related data in the core data files;
    receiving by the first processing system non-core data files from a non-core system, the non-core data files containing second health-related data for the individual;
    loading by the first processing system the extracted non-core data files, including the second health-related data for the individual, into the staging database;
    determining whether the individual has opted out of analytical processing of any portion of the second health-related data in the non-core data files;
    matching by the first processing system staged first and second health-related data from the core and non-core data files to the same individual using one or more matching rules, wherein opted-out portions of the first and second health related data are excluded from the matching;
    compressing by the first processing system the matched first and second health-related data for the individual into at least one compressed file, wherein each portion of the matched first and second health-related data in the at least one compressed file is assigned an identical universal individual identifier and the universal individual identifier is unique to the individual;
    providing the at least one compressed file to an analytics engine for performing one or more predetermined analytical processes thereon and creating at least one analytics results file therefrom;
    receiving by a second processing system the at least one analytics results file from the analytics engine and decompressing the at least one analytics results file using the universal individual identifier to access the analytics results for the individual; and
    providing access to the analytics results for the individual to at least one user, wherein the user utilizes the analytics results in a process related to the health of the individual.

2. The process according to claim 1, wherein the non-core system is selected from the group consisting of pharmacy data processors, laboratory data processors and health risk assessment processors.

3. The process according to claim 1, wherein the one or more matching rules include matching a combination of at least two of the following attributes of persons from the staged first and second health-related data: last name, first name, at least part of social security number, year of birth, date of birth, zip code, gender.

4. The process according to claim 3, wherein the one or more matching rules include matching a combination of at least three of the following attributes of persons from the staged first and second health-related data: last name, first name, at least part of social security number, year of birth, date of birth, zip code, gender.

5. The process according to claim 4, wherein the one or more matching rules further include determining a confidence level for proposed matches, wherein staged first and second health-related data matched with a determined confidence level in a first range is assigned the universal individual identifier, staged data matched with a determined confidence level in a second range is not assigned the universal individual identifier, and staged data matched with a determined confidence level in a third range is flagged for manual review to determine whether or not to assigned the universal individual identifier.

6. The process according to claim 1, wherein each of the first and second health-related data include independent identifiers, separate from an assigned universal individual identifier, wherein the independent identifiers identify the first and second health-related data to the core and non-core systems.

7. The process according to claim 1, wherein extracting by the first processing system core data files from the core system, includes at least one of:
    receiving the core data files in response to a pull request from the first processing system to the core system; and
    receiving the non-core data files as a result of a push from the non-core system.

8. The process according to claim 1, wherein receiving by the first processing system non-core data files from the non-core system, includes receiving the non-core data files in response to a request from the first processing system to the non-core system.

9. The process according to claim 1, wherein the receiving by a second processing system the at least one analytics results file from the analytics engine further includes at least one of:

receiving the at least one analytics results file in response to a request from the second processing system to the analytics engine; and receiving the at least one analytics results file as a result of a push from the analytics engine to the second processing system.

10. The process according to claim 1, wherein the second processing system is the non-core system.

11. A process for transforming health-related data for an individual from multiple sources in preparation for health-related analytical processing thereof comprising:

extracting by a first processing system core data files from a core system, the core data files containing medical claims payment data which is separately processed by the core system to determine payment by a payer to a medical service provider for medical services provided to the individual, wherein the core data files also contain first health-related data for the individual;

loading by the first processing system the extracted core data files, including the first health-related data for the individual, into a staging database;

determining whether the individual has opted out of analytical processing of any portion of the first health-related data in the core data files and excluding opted-out portions of the first health-related data from further processing;

receiving by the first processing system non-core data files from a non-core system, the non-core data files containing second health-related data for the individual;

loading by the first processing system the extracted non-core data files, including the second health-related data for the individual, into the staging database;

determining whether the individual has opted out of analytical processing of any portion of the second health-related data in the non-core data files and excluding opted-out portions of the second health-related data from further processing;

compressing by the first processing system the first and second health-related data for the individual into at least one compressed file usable by an analytics engine, wherein each portion of the first and second health-related data in the at least one compressed file is assigned an identical universal individual identifier and the universal individual identifier is unique to the individual; and publishing the at least one compressed file for access by the analytics engine.

12. The process according to claim 11, wherein each of the first and second health-related data include independent identifiers, separate from an assigned universal individual identifier, wherein the independent identifiers identify the first and second health-related data to the core and non-core systems.

13. The process according to claim 11, wherein extracting by the first processing system core data files from the core system, includes at least one of:

receiving the core data files in response to a pull request from the first processing system to the core system; and receiving the non-core data files as a result of a push from the non-core system.

14. The process according to claim 11, wherein receiving by the first processing system non-core data files from the non-core system, includes receiving the non-core data files in response to a request from the first processing system to the non-core system.

15. The process according to claim 11, wherein the first and second health-related data for the individual are compressed by the first processing system into two separate files, the first health-related data being compressed in a first compressed file and the second health-related data being compressed in a second compressed file; and further wherein the first and second compressed files are published for access by the analytics engine.

16. The process according to claim 11, further comprising:

performing by the analytics engine an analytical processes using at least a portion of the first and second health-related data and creating at least one analytics results file therefrom; and receiving by a second processing system the at least one analytics results file from the analytics engine and decompressing the at least one analytics results file using the universal individual identifier to access the analytics results for the individual.

17. The process according to claim 16, wherein the receiving by a second processing system the at least one analytics results file from the analytics engine further includes at least one of:

receiving the at least one analytics results file in response to a request from the second processing system to the analytics engine; and receiving the at least one analytics results file as a result of a push from the analytics engine to the second processing system.

18. The process according to claim 16, wherein the second processing system is the non-core system.

* * * * *